United States Patent
Mathew et al.

(10) Patent No.: US 6,720,429 B2
(45) Date of Patent: Apr. 13, 2004

(54) THIOCARBONYLTHIO COMPOUND AND LIVING FREE RADICAL POLYMERIZATION USING THE SAME

(75) Inventors: Lizamma Mathew, Hsinchu (TW); Kuo-Chen Shih, Kaohsiung (TW)

(73) Assignee: Industrial Technology Research Institute, Hsinchu (TW)

( * ) Notice: Subject to any disclaimer, the term of this patent is extended or adjusted under 35 U.S.C. 154(b) by 92 days.

(21) Appl. No.: 10/128,246

(22) Filed: Apr. 24, 2002

(65) Prior Publication Data

US 2003/0208012 A1 Nov. 6, 2003

(51) Int. Cl.$^7$ .......................................... C07D 209/44
(52) U.S. Cl. ..................................... 548/479
(58) Field of Search .......................... 548/479

(56) References Cited

FOREIGN PATENT DOCUMENTS

EP          0910587     *  12/2001

* cited by examiner

Primary Examiner—Robert W. Ramsuer
Assistant Examiner—Andrea D. Small
(74) Attorney, Agent, or Firm—Sughrue Mion, PLLC

(57) ABSTRACT

The present invention provides a thiocarbonylthio compound represented by formula (I)

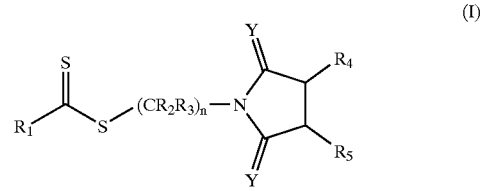

Wherein n is an integer of 0 to 3; $R_1$ is alkyl, haloalkyl, alkenyl, aryl, alkylaryl, haloalkylaryl, arylalkyl, aminoalkyl, alkylamino, alkoxy, alkoxyaryl, alkyl sulfide, or alkylsilyl; $R_2$ and $R_3$ are independently H, alkyl, haloalkyl, alkenyl, aryl, alkylaryl, arylalkyl, aminoalkyl, alkylamino, alkoxy, alkyl sulfide, or alkylsilyl; $R_4$ and $R_5$ are independently H, alkyl, haloalkyl, alkenyl, aryl, alkylaryl, arylalkyl, aminoalkyl, alkylamino, alkoxy, alkyl sulfide, or alkylsilyl, or $R_4$ and $R_5$ link together with the carbon atoms to which they are attached to form a ring system; and Y is O or S. The thiocarbonylthio compound can be used in a living free radical polymerization to obtain a polymer with high conversion and low polydispersity.

13 Claims, No Drawings

THIOCARBONYLTHIO COMPOUND AND LIVING FREE RADICAL POLYMERIZATION USING THE SAME

BACKGROUND OF THE INVENTION

1. Field of the Invention

The present invention relates to a thiocarbonylthio compound, and more particularly to a radical polymerization process for preparing polymers of vinyl monomers with controlled molecular weight and narrow polydispersity in the presence of the thiocarbonylthio compound.

2. Background of the Invention

Radical polymerization is one of the polymerization processes which are most widely exploited industrially because of the variety of the polymerizable monomers (>50% of the commercial polymers), of the ease of application and of the synthesis processes employed (emulsion, suspension, bulk, solution). However, in conventional radical polymerization it is difficult to control the size of the polymer chains and the molecular mass distribution. The polymers thus prepared contain chains of very large and very small masses (broad polydispersity), and this results in materials with uncontrolled properties.

Anionic and cationic polymerization techniques, for their part, allow proper control of the process, but the reaction conditions which these polymerization methods require are not always capable of being implemented on an industrial scale. In addition, many monomers cannot be polymerized using these techniques.

Living free radical polymerization is a recently developed technique for the controlled polymerization of vinyl monomers. The significant advantages of this technique permits the preparation of a wide range of different materials which are either difficult to prepare, or not available by other polymerization processes. The architecture, composition of the backbone, inclusion of functionality, and high degree of control over the molecular weight and polydispersity can be achieved by living free radical polymerization.

WO 98/01478 have reported a process of living free radical polymerization which teaches that in the presence of a suitable thiocarbonylthio compound (Z—C(=S)—S—R, RAFT-agent) to an otherwise conventional free radical polymerization. The so-called RAFT is the abbreviation of reversible addition-fragmentation chain transfer. A polymer with narrow molecular weight distribution can be obtained and the polymer chain length can be freely controlled.

This invention relates to a new thiocarbonylthio system, resulting in a much faster rate for vinyl monomers while still retaining a high degree of control over the molecular weight and polydispersity.

SUMMARY OF THE INVENTION

The object of the present invention is to provide a thiocarbonylthio compound.

Another object of the present invention is to provide a thiocarbonylthio compound that can control the radical polymerization of vinyl monomers in a quasi-living manner. Thiocarbonylthio compound of the present invention enhances the rate of polymerization while maintaining low polydispersity.

To achieve the above-mentioned objects, the thiocarbonylthio compound of the present invention is represented by formula (I)

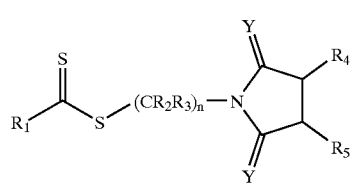

Wherein
n is an integer of 0 to 3;
$R_1$ is alkyl, haloalkyl, alkenyl, aryl, alkylaryl, haloalkylaryl, arylalkyl, aminoalkyl, alkylamino, alkoxy, alkoxyaryl, alkyl sulfide, or alkylsilyl;
$R_2$ and $R_3$ are independently H, alkyl, haloalkyl, alkenyl, aryl, alkylaryl, arylalkyl, aminoalkyl, alkylamino, alkoxy, alkyl sulfide, or alkylsilyl;
$R_4$ and $R_5$ are independently H, alkyl, haloalkyl, alkenyl, aryl, alkylaryl, arylalkyl, aminoalkyl, alkylamino, alkoxy, alkyl sulfide, or alkylsilyl, or $R_4$ and $R_5$ link together with the carbon atoms to which they are attached to form a ring system; and
Y is O or S.

The living free radical polymerization process of the present invention includes polymerizing at least one kind of vinyl monomer in the presence of the thiocarbonylthio compound represented by formula (I).

DETAILED DESCRIPTION OF THE INVENTION

The present invention provides a thiocarbonylthio compound represented by formula (I)

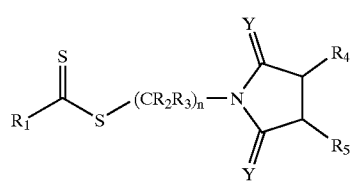

Wherein
n is an integer of 0 to 3;
$R_1$ is alkyl, haloalkyl, alkenyl, aryl, alkylaryl, haloalkylaryl, arylalkyl, aminoalkyl, alkylamino, alkoxy, alkoxyaryl, alkyl sulfide, or alkylsilyl;
$R_2$ and $R_3$ are independently H, alkyl, haloalkyl, alkenyl, aryl, alkylaryl, arylalkyl, aminoalkyl, alkylamino, alkoxy, alkyl sulfide, or alkylsilyl;
$R_4$ and $R_5$ are independently H, alkyl, haloalkyl, alkenyl, aryl, alkylaryl, arylalkyl, aminoalkyl, alkylamino, alkoxy, alkyl sulfide, or alkylsilyl, or $R_4$ and $R_5$ link together with the carbon atoms to which they are attached to form a ring system; and
Y is O or S.

Alkyl referred to in the present invention may contain from 1 to 18, preferably from 1 to 10, carbon atoms. Haloalkyl may have 1 to 18, preferably from 1 to 10, carbon atoms. An example is chloromethyl (—$CH_2Cl$). Aryl may have 6 to 10 carbon atoms, such as phenyl. Alkylaryl or arylalkyl may have 7 to 20, preferably from 7 to 15, carbon atoms. An example of alkylaryl is methylphenyl (—$C_6H_4$—$CH_3$), and an example of arylalkyl is phenylmethyl (—$CH_2$—$C_6H_5$). Haloalkylaryl may have 7 to 20, preferably from 7 to 15, carbon atoms. An example of haloalkylaryl is trifluoromethylphenyl.

Aminoalkyl referred to in the present invention may contain from 1 to 18, preferably from 1 to 10, carbon atoms. The aminoalkyl may be primary, secondary, or tertiary. Examples include aminomethyl (—CH$_2$—NH$_2$), methylaminomethyl (—CH$_2$—NH(CH$_3$)), and dimethylaminomethyl (—CH$_2$—N(CH$_3$)$_2$).

Alkylamino referred to in the present invention may contain from 1 to 18, preferably from 1 to 10 carbon atoms. The alkylamino may be secondary or tertiary. Examples include methylamino (—NH—CH$_3$) and dimethylamino (—N(CH$_3$)$_2$).

Alkoxy referred to in the present invention may contain from 1 to 18, preferably from 1 to 10, carbon atoms. Examples include methoxy and ethoxy. Alkoxyaryl referred to in the present invention may contain from 7 to 24, preferably from 7 to 16 carbon atoms. An example of alkoxyaryl is methoxyphenyl.

Alkyl sulfide may contain from 1 to 18, preferably from 1 to 10, carbon atoms. An example is methyl sulfide (—S—CH$_3$). Alkylsilyl may contain from 1 to 20, preferably from 1 to 10, carbon atoms. Examples include trimethylsilyl (—Si(CH$_3$)$_3$), dimethylsilyl (—SiH(CH$_3$)$_2$), and dimethylethylsilyl (—Si(CH$_3$)$_2$(C$_2$H$_5$)).

Preferably, $R_1$ is alkyl, aryl, alkylaryl, alkoxyaryl, or haloalkylaryl, and $R_2$ and $R_3$ are independently H, alkyl, haloalkyl, alkenyl, aryl, alkylaryl, or arylalkyl.

$R_4$ and $R_5$ can be independently H, alkyl, haloalkyl, alkenyl, aryl, alkylaryl, arylalkyl, aminoalkyl, alkylamino, alkoxy, alkyl sulfide, or alkylsilyl, and preferably H, alkyl, haloalkyl, alkenyl, aryl, alkylaryl, or arylalkyl. Or, alternatively, $R_4$ and $R_5$ can link together with the carbon atoms to which they are attached to form a ring system having from 4 to 20 carbon atoms. The ring system can be a saturated ring or an unsaturated ring such as an aromatic ring.

According to a preferred embodiment of the present invention, the thiocarbonylthio compound of the present invention can be represented by formula (II),

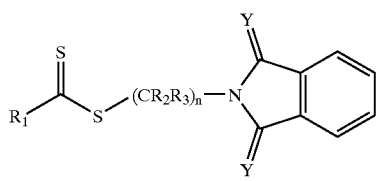

(II)

Wherein n is an integer of 0 to 3;

$R_1$ is alkyl, haloalkyl, alkenyl, aryl, alkylaryl, haloalkylaryl, arylalkyl, aminoalkyl, alkylamino, alkoxy, alkoxyaryl, alkyl sulfide, or alkylsilyl;

$R_2$ and $R_3$ are independently H, alkyl, haloalkyl, alkenyl, aryl, alkylaryl, arylalkyl, aminoalkyl, alkylamino, alkoxy, alkyl sulfide, or alkylsilyl;

Y is O or S.

Compared to the thiocarbonylthio compounds reported in WO 98/01478, the above thiocarbonylthio compound is easy to synthesize and obtained as crystals in high yield. No further purification method like column chromatography is required.

In the presence of the thiocarbonylthio compound represented by formula (I) of the present invention, the polymerization has living characteristics and provides polymers of controlled molecular weight and low polydispersity.

The monomer that is polymerized can be one vinyl monomer alone, or in combination with one or more polymerizable vinyl comonomers.

Specific monomers include the followings: acrylic acid and its salts, acrylates, methacrylic acid and its salts, methacrylates, acrylonitriles, styrenes, acrylamides, butadiene, isoprene or mixtures thereof. Representative examples include methyl acrylate, ethyl acrylate, propyl acrylate (all isomers), butyl acrylate (all isomers), 2-ethylhexyl acrylate, 2-hydroxyethyl acrylate, isobornyl acrylate, acrylic acid, benzyl acrylate, phenyl acrylate, acrylonitrile, styrene, N,N-dimethylaminoethyl methacrylate, methacrylamides, acrylamides, N-isopropyl acrylamide, methyl methacrylate etc.

In the presence of the thiocarbonylthio compound represented by formula (I), together with a free radical initiator, the molecular weight of the polymer obtained can be predetermined. The polydispersity of the polymer obtained is usually in a range from 1.05 to 2, and preferably decreased to a range from 1.05 to 1.5, and more preferably decreased to a range from 1.05 to 1.3.

The compound capable of generating free radicals suitable for use in the present invention is not limited and can be any suitable for use in the conventional free radical polymerization, such as AIBN, diacyl peroxides, and di-tert-butyl peroxide.

Using the present invention, the polymer obtained can be a homopolymer or a copolymer. Various copolymers with a well-defined structure can be obtained, including (1) block copolymers (two or more blocks) with narrow polydispersity, (2) graft copolymers with narrow polydispersity, (3) gradient copolymers, (4) star copolymers, and (5) hyperbranched copolymers. Various polymers with a terminal functional group can also be prepared. The emergence of various novel polymers can provide new materials with new physical properties to be applied in industry. This will not only enhance the performance of the existing products, but also speed up the development of new products. The polymeric materials developed in the present invention can be applied in many fields, including dispersants such as pigment dispersants in ink, photoresists, surfactants, surface treating agents, adhesives, rheology controllers, coatings, and thermoplastic elastomers.

The following examples are intended to illustrate the process and the advantages of the present invention more fully without limiting its scope, since numerous modifications and variations will be apparent to those skilled in the art.

Synthesis of Thiocarbonylthio Compound

The thiocarbonylthio compounds obtained from the following Examples 1–4 have the following formula (1):

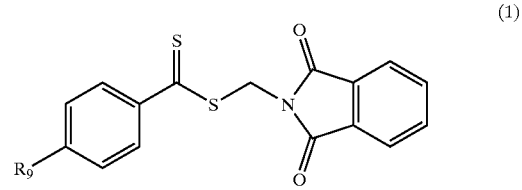

(1)

$R_9$=H (1a), methyl (1b), methoxy (1c), trifluoromethyl (1d)

The reactions of Examples 1–4 are shown below.

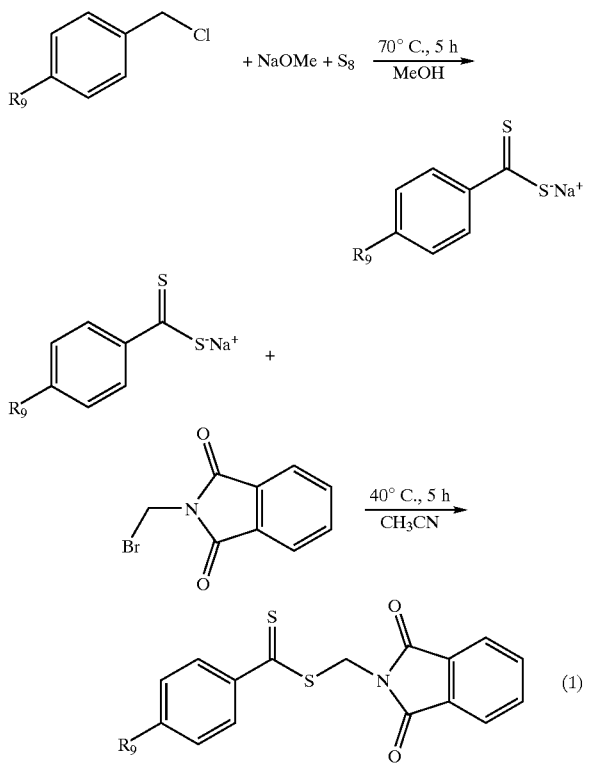

EXAMPLE 1
Synthesis of (1a)

To a mixture of methanol (15 mL), sulfur (0.06mol, 1.92 g) and sodium methoxide solution (30% in methanol, 12 mL), was added dropwise benzyl chloride (0.03 mol, 3.8 g) within one hour. The reaction mixture was allowed to heat at 70° C. for 5 hours. After removal of the volatiles in vacuum, the resulting dithiobenzoic acid salt was dissolved in acetonitrile (200 ml). N-(bromomethyl) phthalimide (0.03 mol, 7.2 g) was added and the reaction mixture was heated at 70° C. for 5 h. The hot solution was filtered to remove the white solid. Evaporation of the solvent gave the product in 80% yield as red crystals(1a). Yield: 80% $^1$H NMR (CDCl$_3$) (ppm): 5.6(s, 2H), 7.31–7.38 (m, 2H), 7.47–7.51(m, 1H), 7.71–7.74 (m, 2H), 7.86–7.96(m, 4H).

EXAMPLE 2
Synthesis of (1b)

To a mixture of methanol (15 mL), sulfur (0.06 mol, 1.92 g) and sodium methoxide solution (30% in methanol, 12 mL), was added dropwise p-methyl benzyl chloride (0.03 mol, 4.22 g) within one hour. The reaction mixture was allowed to heat at 70° C. for 5 hours. After removal of the volatiles in vacuum, the resulting dithiobenzoic acid salt was dissolved in acetonitrile (200 mL). N-(Bromomethyl) phthalimide (0.03 mol, 7.2 g) was added and the reaction mixture was heated at 70° C. for 5 h. After workup, the crude product was recrystallized as light orange crystals(1b). Yield:55%. $^1$H NMR (CDCl$_3$) (ppm): 2.34(s, 3H), 5.6(s, 2H), 7.14(d, 2H), 7.71–7.74(m, 2H), 7.85–7.9(m, 4H)

EXAMPLE 3
Synthesis of (1c)

To a mixture of methanol (15 mL), sulfur (0.06 mol, 1.92 g) and sodium methoxide solution (30% in methanol, 12 mL), was added dropwise p-methoxy benzyl chloride (0.03 mol, 4.62 g) within one hour. The reaction mixture was allowed to heat at 70° C. for 5 hours. After removal of the volatiles in vacuum, the resulting dithiobenzoic acid salt was dissolved in acetonitrile (200 mL). N-(Bromomethyl) phthalimide (0.03 mol, 7.2 g) was added and the reaction mixture was heated at 70° C. for 5 h. The hot solution was filtered to remove the white solid. Evaporation of the solvent gave the product in 70% yield as orange crystals(1a) $^1$H NMR (CDCl$_3$) (ppm): 3.8(s, 3H), 5.6(s, 2H, —CH$_2$), 6.9(d, 2H), 7.7(m, 2H), 7.9(d, 2H), 8.0(d, 2H).

EXAMPLE 4
Synthesis of (1d)

To a mixture of methanol (15 mL), sulfur (0.02 mol, 1.92 g) and sodium methoxide solution (30% in methanol, 4 mL), was added dropwise p-trifluoromethyl benzyl chloride (0.01 mol) within one hour. The reaction mixture was allowed to heat at 70° C. for 5 hours. After removal of the volatiles in vacuum, the resulting dithiobenzoic acid salt was dissolved in acetonitrile (40 mL). N-(Bromomethyl) phthalimide (0.01 mol, 1.95 g) was added and the reaction mixture was heated at 70° C. for 5 h. The hot solution was filtered to remove the white solid. Evaporation of the solvent gave the product in 90% yield. $^1$H NMR (CDCl$_3$) (ppm): 5.6(s, 2H, —CH$_2$), 7.6(d, 2H), 7.84(m, 2H), 7.9(m, 2H), 8.0(d, 2H).

EXAMPLE 5
Synthesis of (2a)

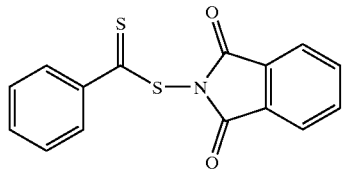

To a mixture of methanol (15 mL), sulfur (0.06 mol) and sodium methoxide solution (30% in methanol, 12 mL), was added dropwise benzyl chloride (0.03 mol) within one hour. The reaction mixture was allowed to heat at 70° C. for 5 hours. After removal of the volatiles in vacuum, the resulting dithiobenzoic acid salt was dissolved in acetonitrile (200 mL). N-Bromo phthalimide (0.03 mol) was added and the reaction mixture was heated at 70° C. for 5 h. The hot solution was filtered to remove the white solid. Evaporation of the solvent gave the product in 80% yield. $^1$H NMR (CDCl$_3$) (ppm): 7.4(m, 2H), 7.8(m, 1H), 7.9(m, 2H), 8.0(m, 4H).

Synthesis of Low Polydispersity Polymer
General Experimental Conditions

Monomers were purified to remove inhibitors prior to use. Degassing was accomplished by freeze-pump-thaw cycles. Molecular weights and molecular weight distribution of the polymers were obtained by gel permeation chromatography with Waters Ultra-styragel columns with THF as eluent and calibrated with polystyrene standards.

EXAMPLE 6
Preparation of Low Polydispersity Poly (t-butyl acrylate) Using (1a)

t-Butyl acrylate (3.75 mL), toluene (1.25 mL), azobisisobutyronitrile (3.9 mg) and compound (1a) (14.7 mg) were placed in a Schlenk tube. The solution was degassed through four freeze-pump-thaw cycles prior to being heated at 60° C. for 16 h. The conversion based on the weight of the polymer obtained is 70%. $M_n$ is 49613, and $M_w/M_n$ is 1.29.

EXAMPLE 7
Preparation of Low Polydispersity Poly (t-butyl acrylate) Using (1b)

t-Butyl acrylate (3.75 mL), toluene (1.25 mL), azobisisobutyronitrile (3.9 mg) and compound (1b) (15.3 mg) were placed in a Schlenk tube. The solution was degassed through four freeze-pump-thaw cycles prior to being heated at 60° C. for 16 h. 90% conversion based on weight of the polymer obtained. $M_n$ is 70845; $M_w/M_n$ is 1.26.

EXAMPLE 8
Preparation of Low Polydispersity Poly (t-butyl acrylate) Using (1c)

t-Butyl acrylate (3.75 mL), toluene (1.25 mL), azobisisobutyronitrile (3.8 mg) and compound (1c) (16.4 mg) were placed in a Schlenk tube. The solution was degassed through four freeze-pump-thaw cycles prior to being heated at 60° C. for 16 h. >95% conversion based on weight of the polymer obtained. $M_n$ is 67502; $M_w/M_n$ is 1.24.

Comparative Example 1

The same procedures described in Example 6 were performed except that compound (1a) was replaced by the following compound (V), which is a chain transfer agent used in WO 98/01478. The polymer obtained has conversion 42%, $M_n$ 34614, and $M_w/M_n$ 1.33, with a higher molecular weight shoulder.

It can be seen that by using (1a), (1b) or (1c) of the present invention, the conversion is increased, and polydispersity ($M_w/M_n$) is lowered.

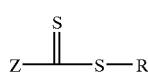

(V)

Z is phenyl, and R is —C(CH$_3$)$_2$CN

EXAMPLE 9
Preparation of Low Polydispersity Poly (methyl acrylate) Using (1c)

Methyl acrylate (3.75 ml), toluene (1.25 ml), azobisisobutyronitrile (3.8 mg) and compound (1c) (16.4 mg) were placed in a Schlenk tube. The solution was degassed through four freeze-pump-thaw cycles prior to being heated at 60° C. for 16 h. >90% conversion based on weight of the polymer obtained. $M_n$ is 71624, and $M_w/M_n$ is 1.31.

Comparative Example 2

The same procedures described in Example 9 were performed except that compound (1c) was replaced by compound (V). The polymer obtained has conversion 47%, $M_n$ 33813, and $M_w/M_n$ 1.35, with a high molecular weight shoulder.

It can be seen that by using (1c) of the present invention, the conversion is increased, and polydispersity is lowered.

EXAMPLE 10
Preparation of Low Polydispersity Poly (t-butyl acrylate) Using (1d)

t-Butyl acrylate (3.75 mL), toluene (1.25 mL), azobisisobutyronitrile (3.8 mg) and compound (1d) (16.4 mg) were placed in a Schlenk tube. The solution was degassed through four freeze-pump-thaw cycles prior to being heated at 60° C. for 8 h. 34% conversion based on weight of the polymer obtained. $M_n$ is 23376; $M_w/M_n$ is 1.12.

EXAMPLE 11
Preparation of Low Polydispersity Poly (methyl acrylate) Using (1d)

Methyl acrylate (3.75 mL), toluene (1.25 mL), azobisisobutyronitrile (3.8 mg) and compound (1d) (16.4 mg) were placed in a Schlenk tube. The solution was degassed through four freeze-pump-thaw cycles prior to being heated at 60° C. for 8 h. 25% conversion based on weight of the polymer obtained. $M_n$ is 17493; $M_w/M_n$ is 1.10.

EXAMPLE 12
Preparation of Low Polydispersity Poly (acrylic acid) Using (1c)

Acrylic acid (3.75 mL), DMF (1.25 mL), azobisisobutyronitrile (3.84 mg) and compound (1c) (16.1 mg) were placed in a Schlenk tube. Degassing progressed through four freeze-pump-thaw cycles. >90% conversion based on weight of the polymer obtained. A little portion of the polymer was methylated before injecting into GPC. $M_n$ is 76791, $M_w/M_n$ is 1.28.

EXAMPLE 13
Preparation of Low Polydispersity Poly (styrene) Using (1c)

Styrene (5 mL) and compound (1c) (16.0 mg) were placed in a Schlenk tube, degassed through four freeze-pump-thaw cycles and polymerized at 110° C. for 16 h. 33% conversion based on weight of the polymer obtained. $M_n$ 32864, and $M_w/M_n$ 1.20.

EXAMPLE 14
Preparation of Low Polydispersity Poly (styrene) Using (1a)

Styrene (5 mL) and compound (1a) (14.6 mg) were placed in a Schlenk tube, degassed through four freeze-pump-thaw cycles and polymerized at 110° C. for 16 h. 34% conversion based on weight of the polymer obtained. $M_n$ 35215, and $M_w/M_n$ 1.22.

EXAMPLE 15
Preparation of Low Polydispersity Poly (styrene) Using (1d)

Styrene (5 mL) and compound (1d) (14.6 mg) were placed in a Schlenk tube, degassed through four freeze-pump-thaw cycles and polymerized at 110° C. for 16 h. 46% conversion based on weight of the polymer obtained. $M_n$ 32448, and $M_w/M_n$ 1.09.

EXAMPLE 16
Preparation of Low Polydispersity Poly (acrylonitrile) Using (1c)

Acrylonitrile (10 mL), compound (1c) (93 mg) and ethylene carbonate (25 g) were placed in a Schlenk tube, degassed through four freeze-pump-thaw cycles and polymerized at 60° C. for 16 h. 64% conversion based on weight of the polymer obtained. $M_n$ 18000(NMR), and $M_w/M_n$ 1.2.

EXAMPLE 17
Preparation of Low Polydispersity Poly (methyl acrylate) Using (2a)

Methyl acrylate (3.75 mL), toluene (1.25 mL), azobisisobutyronitrile (3.8 mg) and compound (2a) (16.4 mg) were placed in a Schlenk tube. The solution was degassed through four freeze-pump-thaw cycles prior to being heated at 60° C. for 8 h. >99% conversion based on weight of the polymer obtained. $M_n$ is 79775; $M_w/M_n$ is 1.4.

EXAMPLE 18
Molecular Weight and Conversion Data for Poly (t-Butyl acrylate) Prepared with (1c).

The experimental conditions described in Example 8 were used for the kinetic runs.

| Entry | Time/hr | Mn | $M_w/M_n$ | Conversion % |
|---|---|---|---|---|
| 1 | 4 | 17083 | 1.13 | 25.2 |
| 2 | 8 | 29988 | 1.15 | 44.4 |
| 3 | 16 | 67502 | 1.24 | >95 |

The easily prepared thiocarbonylthio compounds provide excellent control. The data show that the polymerization can be taken to high conversion with high molecular weight and narrow polydispersity.

The foregoing description of the preferred embodiments of this invention has been presented for purposes of illustration and description. Obvious modifications or variations are possible in light of the above teaching. The embodiments chosen and described provide an excellent illustration of the principles of this invention and its practical application to thereby enable those skilled in the art to utilize the invention in various embodiments and with various modifications as are suited to the particular use contemplated. All such modifications and variations are within the scope of the present invention as determined by the appended claims when interpreted in accordance with the breadth to which they are fairly, legally, and equitably entitled.

What is claimed is:

1. A thiocarbonylthio compound represented by formula (I)

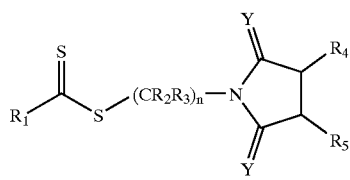

(I)

Wherein n is an integer of 0 to 3;

$R_1$ is alkyl, haloalkyl, alkenyl, aryl, alkylaryl, haloalkylaryl, arylalkyl, aminoalkyl, alkylamino, alkoxy, alkoxyaryl, alkyl sulfide, or alkylsilyl;

$R_2$ and $R_3$ are independently H, alkyl, haloalkyl, alkenyl, aryl, alkylaryl, arylalkyl, aminoalkyl, alkylamino, alkoxy, alkyl sulfide, or alkylsilyl;

$R_4$ and $R_5$ are independently H, alkyl, haloalkyl, alkenyl, aryl, alkylaryl, arylalkyl, aminoalkyl, alkylamino, alkoxy, alkyl sulfide, or alkylsilyl, or $R_4$ and $R_5$ link together with the carbon atoms to which they are attached to form a ring system; and Y is O or S.

2. The compound as claimed in claim 1, wherein $R_1$ is aryl, alkylaryl, alkoxyaryl, or haloalkylaryl.

3. The compound as claimed in claim 1, wherein $R_2$ and $R_3$ are independently H, alkyl, haloalkyl, alkenyl, aryl, alkylaryl, or arylalkyl.

4. The compound as claimed in claim 1, wherein $R_4$ and $R_5$ are independently H, alkyl, haloalkyl, alkenyl, aryl, alkylaryl, arylalkyl, aminoalkyl, alkylamino, alkoxy, alkyl sulfide, or alkylsilyl.

5. The compound as claimed in claim 1, wherein $R_4$ and $R_5$ link together with the carbon atoms to which they are attached to form a ring system having from 4 to 20 carbon atoms.

6. The compound as claimed in claim 5, wherein the ring system is an unsaturated ring.

7. The compound as claimed in claim 6, wherein the ring system is an aromatic ring.

8. The compound as claimed in claim 7, wherein the compound is represented by formula (II),

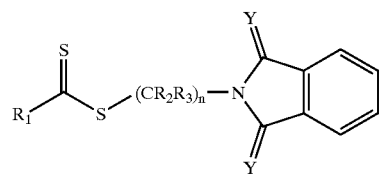

(II)

Wherein n is an integer of 0 to 3;

$R_1$ is alkyl, haloalkyl, alkenyl, aryl, alkylaryl, haloalkylaryl, arylalkyl, aminoalkyl, alkylamino, alkoxy, alkoxyaryl, alkyl sulfide, or alkylsilyl;

$R_2$ and $R_3$ are independently H, alkyl, haloalkyl, alkenyl, aryl, alkylaryl, arylalkyl, aminoalkyl, alkylamino, alkoxy, alkyl sulfide, or alkylsilyl; and Y is O or S.

9. The compound as claimed in claim 8, wherein the compound is

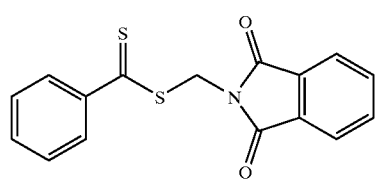

(1a)

10. The compound as claimed in claim 8, wherein the compound is

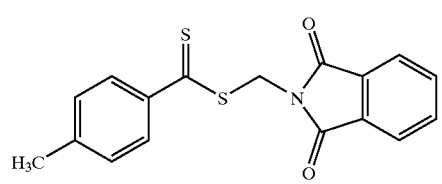

(1b)

11. The compound as claimed in claim 8, wherein the compound is

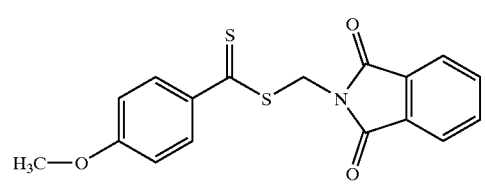

(1c)

12. The compound as claimed in claim 8, wherein the compound is

13. The compound as claimed in claim 8, wherein the compound is
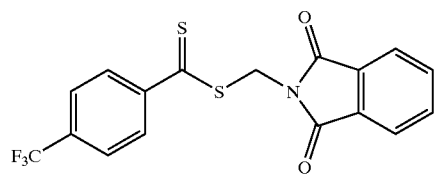
(1d)
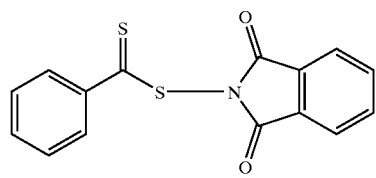
(2a)
* * * * *